(12) United States Patent
Gudnason et al.

(10) Patent No.: US 7,381,860 B2
(45) Date of Patent: Jun. 3, 2008

(54) WOUND DRESSING AND METHOD FOR MANUFACTURING THE SAME

(75) Inventors: Palmar I. Gudnason, Reykjavik (IS); Thordur Elefsen, Mosfellsbaer (IS)

(73) Assignee: hf Ossur, Reykjavik (IS)

( * ) Notice: Subject to any disclaimer, the term of this patent is extended or adjusted under 35 U.S.C. 154(b) by 0 days.

(21) Appl. No.: 11/603,067

(22) Filed: Nov. 22, 2006

(65) Prior Publication Data

US 2007/0066925 A1    Mar. 22, 2007

Related U.S. Application Data

(63) Continuation of application No. 11/339,696, filed on Jan. 26, 2006, now Pat. No. 7,161,056.

(60) Provisional application No. 60/647,398, filed on Jan. 28, 2005, provisional application No. 60/726,174, filed on Oct. 14, 2005.

(51) Int. Cl.
*A61F 13/00* (2006.01)

(52) U.S. Cl. .................. 602/55; 602/41; 602/42; 602/43; 602/46; 602/54

(58) Field of Classification Search ........... 604/304, 604/308; 128/888, 889; 602/41–43, 52, 602/56
See application file for complete search history.

(56) References Cited

U.S. PATENT DOCUMENTS

| | | | |
|---|---|---|---|
| 2,032,923 A | 3/1936 | Eldridge | |
| 3,156,242 A | 11/1964 | Crowe, Jr. | |
| 3,292,619 A * | 12/1966 | Egler | 602/47 |
| 3,307,545 A * | 3/1967 | Surowitz | 602/47 |
| 4,291,072 A | 9/1981 | Barrett et al. | |
| 4,336,279 A | 6/1982 | Metzger | |
| 4,472,461 A | 9/1984 | Johnson | |
| 4,541,426 A | 9/1985 | Webster | |
| 4,614,183 A | 9/1986 | McCracken et al. | |
| 4,657,006 A | 4/1987 | Rawlings et al. | |
| 4,699,146 A | 10/1987 | Sleverding | |
| 4,733,659 A | 3/1988 | Edenbaum et al. | |
| 4,838,253 A | 6/1989 | Brassington | |
| 4,867,150 A | 9/1989 | Gilbert | |
| 4,906,240 A | 3/1990 | Reed et al. | |
| 4,921,704 A | 5/1990 | Fabo | |
| 4,991,574 A | 2/1991 | Pocknell | |
| 5,147,338 A * | 9/1992 | Lang et al. | 604/304 |
| 5,160,328 A | 11/1992 | Cartmell et al. | |

(Continued)

FOREIGN PATENT DOCUMENTS

GB    898 826    6/1962

*Primary Examiner*—Kim M. Lewis
(74) *Attorney, Agent, or Firm*—Bacon & Thomas, PLLC

(57) ABSTRACT

A method for producing a wound dressing wherein a curable silicone mixture is extruded onto a generally planar molding surface. The silicone mixture defines a first surface adjacent the planar surface and a second surface opposite the first surface. The molding surface is heated at a curing temperature sufficient to cause the silicone mixture to cross-link. The silicone mixture is uniformly spread over the molding surface such that the silicone mixture has a generally uniform thickness and the second surface is substantially planar. The second surface of the silicone mixture is laminated to an absorbent material after the silicone mixture has started to cross-link and transform to a gel due to exposure to the heated molding surface.

8 Claims, 6 Drawing Sheets

U.S. PATENT DOCUMENTS

| | | |
|---|---|---|
| 5,209,965 A | 5/1993 | Caldwell |
| 5,244,457 A | 9/1993 | Karami et al. |
| 5,322,729 A | 6/1994 | Heeter et al. |
| 5,340,363 A | 8/1994 | Fabo |
| 5,489,262 A | 2/1996 | Cartmell et al. |
| 5,512,041 A | 4/1996 | Bogart |
| 5,540,922 A | 7/1996 | Fabo |
| 5,591,820 A | 1/1997 | Kydonieus et al. |
| 5,593,395 A | 1/1997 | Martz |
| 5,603,946 A | 2/1997 | Constantine |
| 5,635,201 A | 6/1997 | Fabo |
| 5,653,699 A | 8/1997 | Reed et al. |
| 5,782,787 A | 7/1998 | Webster |
| 5,847,003 A | 12/1998 | Ptchelintsev et al. |
| 5,914,125 A | 6/1999 | Andrews et al. |
| 6,051,747 A | 4/2000 | Lindqvist et al. |
| 6,103,369 A | 8/2000 | Lucast et al. |
| 6,149,614 A | 11/2000 | Dunshee et al. |
| 6,320,093 B1 | 11/2001 | Augustine et al. |
| 6,472,581 B1 | 10/2002 | Muramatsu et al. |
| 6,479,724 B1 | 11/2002 | Areskoug et al. |
| 2003/0040691 A1 | 2/2003 | Griesbach, III et al. |
| 2003/0120229 A1 | 6/2003 | de Jong et al. |
| 2003/0167028 A1 | 9/2003 | Binder et al. |
| 2003/0194526 A1 | 10/2003 | Vesley et al. |
| 2004/0138605 A1 | 7/2004 | Sigurjonsson et al. |

* cited by examiner

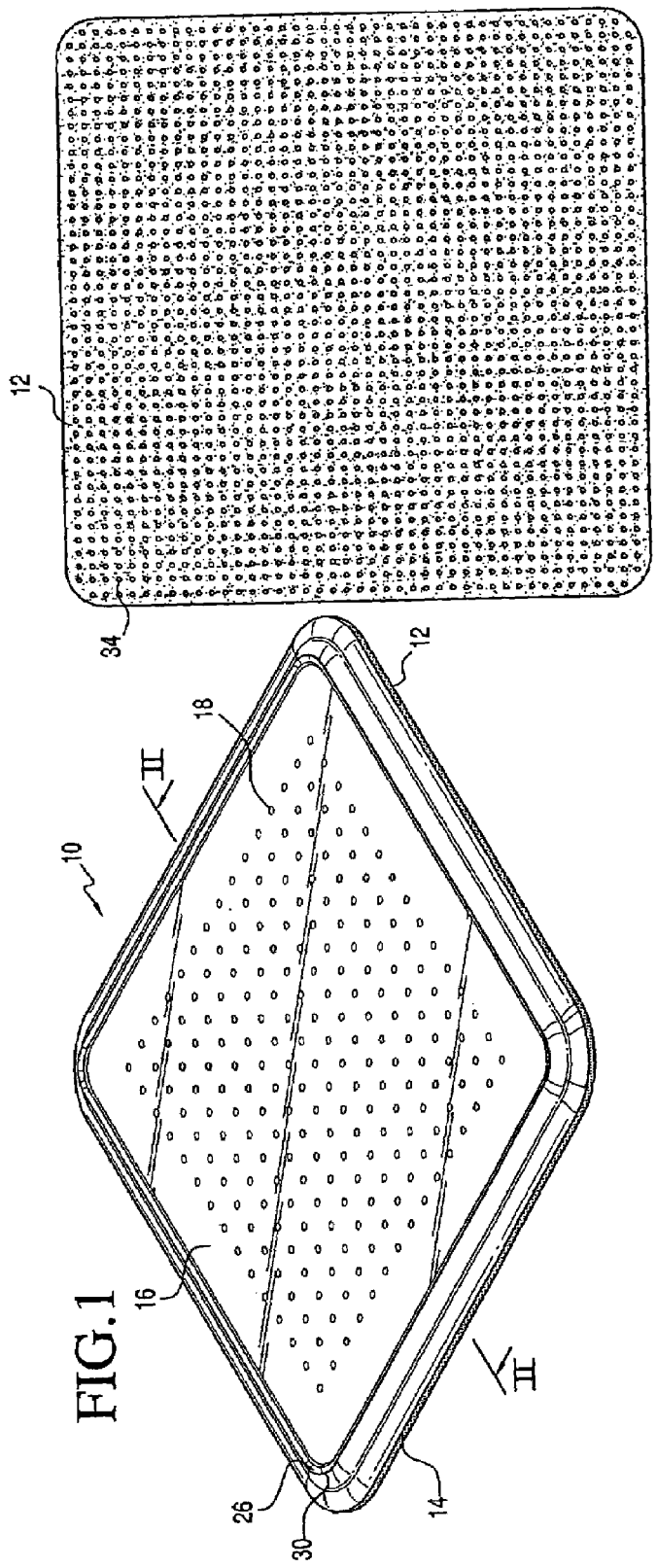
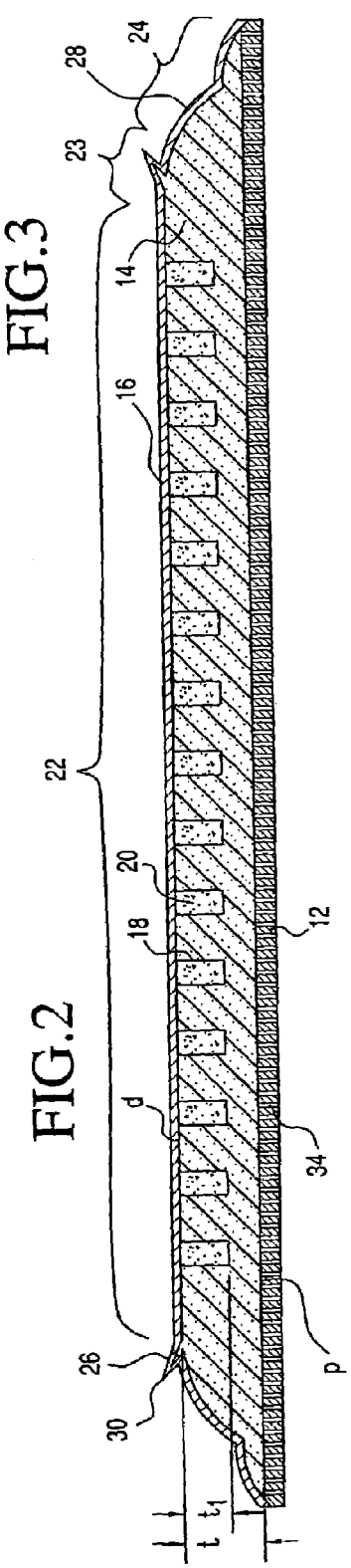

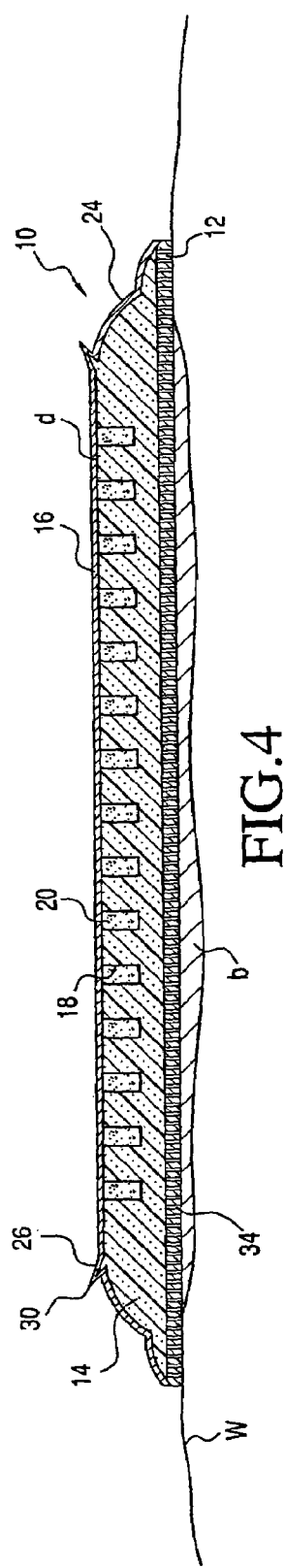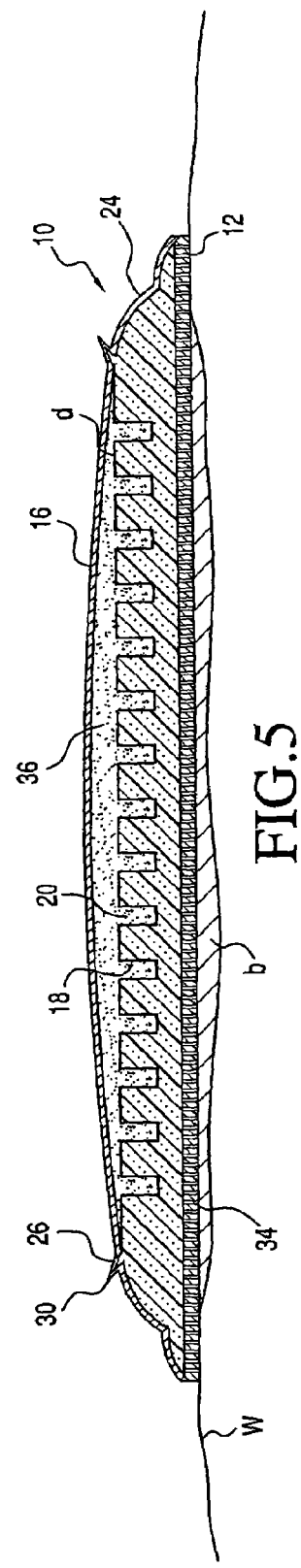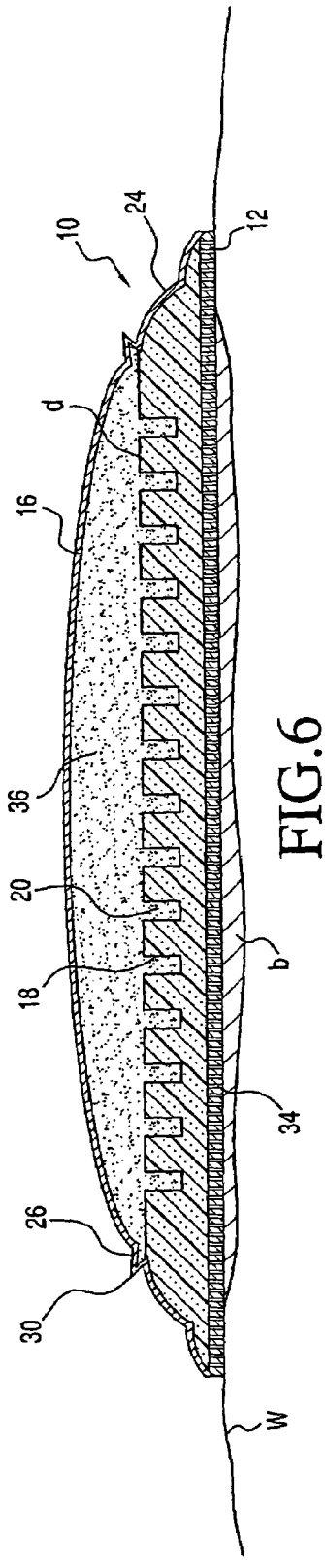

WOUND DRESSING AND METHOD FOR MANUFACTURING THE SAME

This application is a continuation of U.S. application Ser. No. 11/339,696 filed on Jan. 26, 2006 now U.S. Pat. No. 7,161,056, which claims the benefit of U.S. provisional application Nos. 60/647,398, filed Jan. 28, 2005, and 60/726,174, filed 14 Oct. 2005.

BACKGROUND

Historically, many diverse materials of various origins have been used to treat wounds by absorbing wound fluids and tissue, generally referred to as "exudate," from a wound site with some type of absorbent material. In recent years, use of polymeric-based wound care products have become increasingly popular to control wound site environmental factors such as water vapor, oxygen permeability, bacterial impermeability, and absorption of exudate. Such wound care products are tailored to meet specific requirements including conformability to a body portion, selective adherence to a wound bed, and adhesiveness to the skin surrounding the wound site.

Recently, occlusive or moisture-retentive dressings have gained increasing acceptance in treating wounds, in particular pressure sores and ulcers. A wide variety of types of structures are known in the art for use in or as wound dressings, and generally comprise components for receiving, absorbing and retaining exudate. Typically, these dressings include polymeric foams, polymeric films, particulate and fibrous polymers, hydrogels and hydrocolloids. Dressings with at least one of these components promote wound healing by providing a moist environment, while removing excess exudate and toxic components, and further serve as a barrier to protect the wound from secondary bacterial infection. While these known dressings can effectively manage a wound, many have been found to possess certain limitations or disadvantages.

Many of the known dressings have an absorbent layer that comprises hydrophilic polymeric foam. Unfortunately, many hydrophilic polymeric foam dressings possess the disadvantage of being limited in the amount of exudate that may be absorbed. The limit in exudate absorption of the foam is often directly related to its overall geometrical size prior to absorbing a fluid. Typically, hydrophilic foams may expand only to 10-20% of their original size. Another disadvantage to hydrophilic foam dressings is that a certain amount of exudate can be "squeezed" out of the foam due to poor liquid retention. The ability of exudates to be squeezed from the foam, and thus dressing itself, poses a risk of infection and may interfere with the healing of the wound.

Yet another disadvantage with known foam dressings is that absorption of exudate by an absorptive layer, such as foam, in contact with the wound causes the central portion of the applied dressing to swell and push up against the wound. Continued swelling can induce separation of the skin adherent layer from the skin outside the wound area, especially at the border of the wound dressing whereat a "curling" effect may occur. This excessive swelling of the dressing may further lead to leakage of the exudate from the periphery of the dressing, thereby providing a tract for the invasion of pathogenic microorganisms and promoting maceration of the wound site.

In many known dressings, a backing layer is provided that comprises a liquid impervious film that is attached to an absorbent layer to prevent exudate from seeping from the dressing. A difficulty arises during fluid uptake in that as the absorbent layer expands, the backing layer must accommodate the expansion of the absorbent layer without causing curling of the dressing.

One solution has been proposed to include a backing layer that is formed of a thin elastic sheet which is yieldable as the absorbent layer swells. It has been found, however, that a liquid impervious plastic film cannot be made to sufficiently stretch in keeping with the expansion of the absorbent layer, and as a result, the film counteracting with the swelling absorbent layer may produce the aforesaid curling at the border of the dressing.

Another solution has been proposed in which a backing layer is attached to the absorbent foam layer and includes a plurality of wrinkles that substantially flatten as the foam layer swells. While the backing layer may accommodate the expansion of the foam layer, the fluid uptake of this dressing is limited by the expandability of the foam layer itself. Accordingly, due to the limited absorptive capacity of the foam layer, the dressing must be frequently replaced.

Ideally, a dressing must have adhesive properties that enable the dressing to attach to the wound site while being non-toxic to skin and eliciting no allergenic response. Moreover, a dressing should possess the ability to prevent bacteria from entering the wound from the ambient environment while providing a suitable moisture transmission rate.

Many known dressings possess the disadvantage of relying solely on a pressure sensitive adhesive layer to secure the dressing to skin. An example of an adhesive is an acrylate glue. While indeed an acrylate glue securely maintains a dressing over a wound, the glue has a tendency to strip the central portion of the dressing from the wound and thus may damage healing tissue.

Wound dressings have been commercially available that include an absorbent foam layer with a skin adherent layer comprising a coating of silicone gel over a surface of the foam layer. According to one solution described in U.S. Pat. No. 6,051,747, the silicone gel coats portions of the walls of the cells of the foam layer to form a plurality of randomly formed apertures. These apertures are created by capillary action when a curable silicone liquid mixture is applied in an uncured state directly to a surface of the foam layer.

It is important to this solution that the silicone mixture be applied to the foam in a liquid state in order for the silicone mixture to be sucked via capillary action into the end portions of the cells near or at the coated surface of the foam layer. Only if the silicone mixture is liquid will the capillary forces of the foam be sufficient to form apertures since overall the capillary forces produced by the foam layer are small. Moreover, the silicone mixture begins to form a gel only after it has started to cure, or more appropriately, cross-link.

This process of coating a foam layer with a liquid silicone mixture and the curing of the same has many inherent drawbacks. One drawback is that some foam cells may not produce sufficient capillary forces to form apertures through the silicone mixture. Thus, some cells may have corresponding apertures in the silicone gel coating while other cells may lack such apertures. Another drawback is that the apertures of the silicone gel coating are randomly formed which may lead to localized areas that inhibit the uptake of the exudate into the foam. This process does not allow the formation of a predetermined pattern of apertures which are uniformly spaced and sized. Thus, there is an overall lack of control of the size, location and density of the apertures.

Another shortcoming to this process and particular dressing is that the surface roughness of the silicone gel coating is largely dependent upon the surface of the foam to be coated. In the event it is desired to obtain a smooth silicone gel layer to be worn against the skin, this approach fails to yield such a smooth silicone layer.

For the foregoing reasons, there is a demand for an improved wound dressing which prevents wound trauma upon repeated dressing changes, improves the durability and lifetime of the dressing, anatomically conforms to a wound, possesses improved fluid uptake, retention and removal properties, and can be securely maintained on a patient's body. It is thus desired to produce a dressing having an adhesive layer that does not possess the drawbacks of known adhesive layers, and instead, gently adheres and detaches from a wound site while providing superior fluid uptake.

SUMMARY

The present invention is directed to an improved wound dressing possessing superior absorbent capabilities including increased fluid uptake and enhanced retention properties. In an embodiment of the invention, a wound dressing includes an absorbent core defining opposed proximal and distal surfaces. A liquid impervious, vapor permeable backing layer is connected to the distal surface of the absorbent core. A perforated layer of silicone gel is laminated to the proximal surface of the absorbent core.

In a variation of the embodiment, the backing layer is provided with a compliant element defined by a ridge generally concentric with the periphery of the absorbent core and extending outwardly relative to the distal surface of the absorbent core. The incorporation of the compliant element into the backing layer permits enhanced accommodation of the expansion of the wound dressing.

According to another variation of the embodiment, the absorbent core is an open-cell polymeric hydrophilic foam that defines a plurality of receptacles containing discrete portions of a moisture absorbent material. The compliant element is generally positioned near the peripheral border of the dressing and effectively functions as a joint to permit migration of the discrete portions of absorbent material from the absorbent core. When the absorbent core and the absorbent material have absorbed a quantity of moisture, an expandable reservoir is defined between central portions of the backing layer and the absorbent core. This reservoir is formed when the discrete portions of absorbent material have absorbed a quantity of exudate and results from detachment of the central portion of the backing layer from the central portion of the absorbent core due to the swelling and expansion of such absorbent material.

In yet another variation of the embodiment, the silicone gel layer has a plurality of through extending openings arranged in a predetermined pattern irrespective of cells of the absorbent core and is substantially planar along a proximal side thereof.

According to this variation, the openings have a preformed, generally circular cross-section and are arranged in a generally equally spaced. In other variants, the openings may be arranged in a variety of patterns such as those having a greater density in the central portion of the silicone gel layer and different sizes according to the location of such openings relative to the proximal surface of the absorbent core.

Advantages over skin adherent layers of known dressings abound in view of the embodiments of the present invention. Specifically, the silicone gel layer has properties that permit the gel to adhere gently to surrounding skin at the wound site. The silicone gel layer is inherently soft and smooth to the touch, and may flow partly into microscopic cavities and cracks in the skin to create a large contact area over the wound site. The pattern and shape of the openings enable greater control over fluid uptake and provide greater absorbent consistency.

Certain methods and variations thereof may be employed to manufacture the embodiments of the wound dressing of the present invention. One method for producing a dressing includes the step of extruding a curable silicone mixture onto a generally planar molding surface that is heated at a curing temperature sufficient to cause the silicone mixture to cross-link. The silicone mixture is uniformly spread over the molding surface such that the silicone mixture has a generally uniform thickness, and opposed first and second surfaces of the silicone mixture are substantially planar. The second surface of the silicone mixture is laminated to an absorbent material after the second surface of the silicone mixture has started to cross-link due to exposure to the molding surface.

In a feature of the method, the molding surface is a belt that moves and defines a plurality of perforating elements extending from the planar molding surface. The perforating elements have a height that is greater than the thickness of the silicone mixture after it is evenly spread onto the molding surface. The perforating elements form a plurality of openings in the silicone mixture as it cures.

Another feature of the method includes rolling the absorbent material into contact with the second surface of the silicone mixture at a nip area between a pressing roller and the heated moving molding surface. At the stage of laminating the silicone mixture to the absorbent material, the silicone mixture is partially cured due to cross-linking and has a physical state of a very soft elastic solid defined as a silicone gel film. The silicone gel film and absorbent material are bonded together at their mating surfaces at the nip area and the curing of the silicone gel film is completed while the silicone gel film and foam are advanced downstream the from laminating station.

BRIEF DESCRIPTION OF THE DRAWINGS

These and other features, aspects, and advantages of the present invention will become better understood with regard to the following description, appended claims, and accompanying drawings where:

FIG. 1 is perspective view showing an embodiment of a wound dressing.

FIG. 2 is a sectional view of the wound dressing in FIG. 1 taken along line II-II.

FIG. 3 is a bottom plan view of the wound dressing in FIG. 1.

FIGS. 4-6 are sectional views illustrating progressive swelling of the wound dressing in FIGS. 1-2 over a wound site.

DETAILED DESCRIPTION OF VARIOUS EMBODIMENTS

A. Overview

Figure 7:
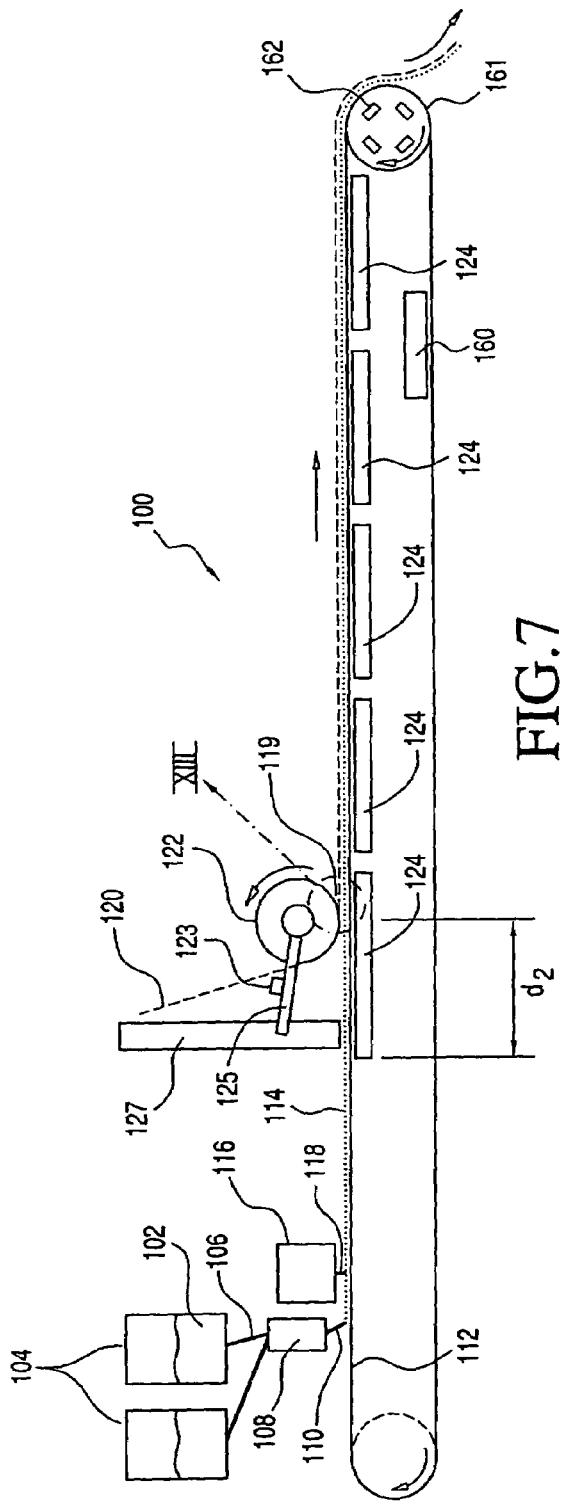
FIGS. 7 and 8 are schematic sectional views illustrating exemplary lamination and finishing sections in the manufacturing process for making a wound dressing according to FIG. 1.

A better understanding of different embodiments of the invention may be had from the following description read in conjunction with the accompanying drawings in which like reference characters refer to like elements.

While the disclosure is susceptible to various modifications and alternative constructions, certain illustrative embodiments thereof are shown in the drawings and will be described below in detail. It should be understood, however, that there is no intention to limit the disclosure to the specific embodiments and methods disclosed, but on the contrary, the intention is to cover all modifications, alternative constructions, combinations, and equivalents falling within the spirit and scope of the disclosure and defined by the appended claims.

It will be understood that, unless a term is expressly defined in this patent to possess a described meaning, there is no intent to limit the meaning of such term, either expressly or indirectly, beyond its plain or ordinary meaning.

B. Environment and Context of Embodiments

Various embodiments of the invention are provided to be used to absorb exudate, combat odor and infection, relieve pain, wound cleanse and maintain a moist environment at a wound surface to facilitate healing of the wound. The embodiments of the invention are particularly configured to absorb exudate or wound fluid, and may therefore be suitable for application for a variety of different wound types.

The various embodiments are conformable to a variety of locations on a living body, and may be dimensioned to accommodate different types and sizes of wounds. Moreover, the adhesive properties may be modified according to the location and type of wound to be treated while taking into consideration the potential for the dressing to cause sensitivity reactions, the ease of application and removal including the production of pain and trauma to wound surfaces, and the interval between wound dressing changes.

Thus, it is to be clearly understood that the various embodiments of the wound dressing according to the invention may be made in any desired sizes and shapes, for example in various standardized sizes and shapes.

The methods described herein for making the various embodiments of the wound dressing may also be modified without departing from the scope of the invention.

While features are shown in the drawing figures that are not described in detail in the description that follows, a detailed description of such features is found in U.S. application Ser. No. 10/725,574 that is incorporated herein by reference.

The descriptions in this application rely upon certain distinctions in the field of polymer science and polymer processing, including the following:

1. Definition of Silicone Gel and Curing of Silicone Gel

This application frequently refers to silicone gels for use as a skin adherent layer. Silicone gels have lightly cross-linked polysiloxane three-dimensional networks. Once suitably cross-linked, silicone gels are solids that retain their form without external containment. The chemical reaction which forms the gel is irreversible.

Prior to curing, a curable silicone mixture is a precursor fluid mixture. The gel reaction is not a linear process. At the point whereat the silicone mixture cures to a gel, a 3-D network is formed and mechanical tests will show that the silicone mixture has transformed into a weak, very soft viscoelastic solid. Further reaction increases the stiffness and strength of the solid, though it remains soft. The reaction is taken to completion so that the product is stable and has no reactive chemical groups. The reaction rate slows towards the end as there are no reactive groups left.

2. Coating Versus Lamination

Of particular importance in this application is the distinction between the manufacturing processes of coating and lamination. Polymer processors consider coating and laminating as distinct processes, and this application relies on their distinction.

The process of coating involves covering a solid substrate with a fluid that may become a solid after it has covered the substrate. The fluid is intended to flow onto the substrate and wet the entire surface evenly. For porous substrates, it also enters, at least in part, interstices of the uneven surface. These phenomena are important contributors to adhesion.

On the contrary, the process of lamination involves the combination of two solid substrates that are adhered to one another. These two substrates may be passed through a nip which applies pressure to the substrates and improves their adherence. Typically, these substrates are bonded to one another with an adhesive, or in the alternative, at least one of the substrates has a sufficient cohesive strength and the necessary adhesive strength to bond sufficiently to the other substrate.

C. Description of Embodiments and Methods for Making the Same

In the following description, basic embodiments and the components of the wound dressing of the application are disclosed. In addition, methods for making the embodiments of the application are provided which would enable a skilled artisan to make the inventive embodiments.

1. Various Embodiments of the Wound Dressing

As shown in FIGS. 1 and 2, an embodiment of the wound dressing 10 includes a perforated silicone gel layer 12 laminated onto a hydrophilic foam absorbent core 14, and a liquid impervious, moisture permeable backing layer 16 secured to the absorbent core 14. The wound dressing depicted in FIG. 1 is in a dry state substantially devoid of moisture.

As more fully exemplified in FIG. 2, the absorbent core 14 defines a proximal surface p that is intended to face towards a wound surface w and a distal surface d that is opposed to the proximal surface p and faces away from a wound surface. In a basic configuration, the silicone gel layer 12 is laminated to the proximal surface p of the absorbent core 14, and the backing layer 16 is attached and sealed to at least part of the distal surface d of the absorbent core 14.

In this embodiment, the absorbent core 14 defines a plurality of receptacles 18 arranged in a predetermined pattern wherein the receptacles 18 are defined as a repeating series of cylindrical compartments. As shown in FIG. 2, the receptacles 18 open at the distal surface d of the absorbent core 14 and extend a distance into the absorbent core 14 a distance $t_1$, short of its entire thickness t.

The receptacles may assume a variety of configurations and, according to one variation, may be cylindrical in shape, and extend transversely along at least a portion of the distal surface of the absorbent core. The plurality of receptacles 18 contain discrete portions of absorbent material 20 that absorb exudate from the wound site and migrate from the receptacles 18 towards the backing layer 16 upon absorption of such exudate.

As illustrated in FIG. 2, the absorbent core 14 generally defines central, intermediate and border portions 22, 23, 24. According to this embodiment, the backing layer 16 is secured to the border portion 24 of the absorbent core 14. The border portion 24 includes a bevel 28 defined near or along a peripheral edge thereof and is provided to retain any loose absorbent material 20 from the receptacles 18 within the dressing 10. In other variations, the absorbent core is devoid of a bevel and the periphery of the absorbent core has the thickness t generally corresponding to the thickness of the central portion 22. In these variations, the backing layer 16 is secured to the edges of the absorbent core 14.

In this embodiment, the backing layer 16 has portions that are lightly laminated to the distal surface d of the absorbent core 14. These portions are laminated to the extent that they separate from the absorbent core 14 after fluid travels to the distal surface of the absorbent core 14 and the absorbent material 20 swells.

The backing layer 16 includes a compliant element 26 that is interposed between the central and border portions 22, 24 of the absorbent core 14. The compliant element 26 is substantially concentric with the central portion 22 and comprises a portion of the backing layer 16 that is not adhered to the absorbent core 14.

According to this variation, the compliant element 26 includes at least one concentric ridge 30. It will be understood that the compliant element may assume a variety configurations. For example, the orientation of the compliant element may be arranged in a variety of directions such as the ridge extending in a range of directions from being generally parallel to the absorbent core on the border portion side of the compliant element to being generally parallel to the absorbent core on the central portion side of the compliant element.

The silicone gel layer 12 is secured to the proximal surface p of the absorbent core 14. The silicone gel layer 12 includes a plurality of openings 34 that are preformed in a pattern prior to securing to the absorbent core 14.

As shown schematically in FIGS. 2 and 3, the plurality of openings 34 may be arranged in a predetermined pattern. The plurality of openings 34 may be configured to correspond to regions near or at the plurality of receptacles 18 of the absorbent core 14 so as to transport exudate from a wound site to the absorbent core 14.

The silicone gel layer 12 is preferably laminated only to the proximal surface p of the absorbent core 14 and does not coat the walls of the pores or holes of the absorbent core 14 defined near the proximal surface p. It will be understood, however, that portions of the silicone gel layer may bulge into irregularities of the absorbent core.

In this instance, it is important to note that any bulging of the silicone gel layer into the absorbent core is due, at least in part, to the pressure exerted against the silicone gel layer and the absorbent core as they are laminated against one another. This bulging phenomena is in contradistinction to when a liquid mixture is used to coat a foam. During coating, the liquid layer wets the walls of foam cells and holes and, as a result of capillary forces, is drawn into the cells of the foam.

2. Operation of Wound Dressing

While not wishing to be bound by a particular mechanism of operation, the present invention is intended to function as a dressing 10 in the manner depicted in FIGS. 4 to 6, after application of the dressing to an exuding skin wound. It will be understood that in the context of the invention, the terms fluid, moisture and exudate are used interchangeably regarding wounds and wound dressings.

The dressing 10 is placed onto a wound site w with the facing layer 12 directed over the wound bed b. The facing layer 12 may adhere to the intact skin around the wound site w as well as to the wound bed b. The dressing 10 is maintained in close apposition to the wound bed b in part by the capillary action of the exudate entering the absorbent core 14 and by the facing layer 12.

As illustrated in FIG. 4, fluid exuded by the wound bed b will be drawn through the apertures 34 towards the absorbent core 14, and the absorbent material 20 contained in the receptacles 18. After being applied over the wound site w for an extended period of time, the applied dressing 10 may appear as shown in FIG. 5 with a slightly enlarged domed, reservoir configuration 36 extending over the central portion of the absorbent core 14. The reservoir 36 is caused by the absorbent material 20 that has absorbed a desired quantity of exudate from the receptacles 18 and discrete portions thereof have swelled and migrated from the receptacles, thereby causing distension of the backing layer 16.

The swollen exudate-laden discrete portions of absorbent material 20 cause the backing layer 16 to detach from the distal surface d of the absorbent core 14 in a predictable manner and to distend upwardly to further permit continued absorbing and swelling of the dressing 10 over the wound site w. In addition, the absorbent core 14 will expand or swell both transversely and longitudinally, and the area of absorbent core 14 will generally increase with increased fluid absorption.

While the backing layer 16 remains sealed along the border portion of the dressing 10, the reservoir 36 is formed such that it is defined between the backing layer 16 and the distal surface d of the absorbent core 14, and sealed along the border portion 24. The reservoir 36 permits the migration of the swollen discrete portions of absorbent material 20 from the receptacles 18 and greatly expands the retention of fluid from the wound bed b. The compliant element 26 effectively functions as a flexible joint for the backing layer 16 by permitting additional expansion of the backing layer 16 in providing additional flexibility and expansion of the backing layer 16 due to the swelling of the absorbent material 20.

As shown in FIG. 6, the dressing 10 has nearly reached its swelling capacity and the backing layer 16 has distended to its maximum. Most notably, at this advance stage of swelling, the border portion 24 of the dressing 10 remains attached to the wound site w due to the provision of the compliant element 26 which compensates for the expansion and swelling of the absorbent core 14 and the absorbent material 20, and the distension of the backing layer 16. It will be further noted that the ridge 30 generally does not fully flatten relative to adjacent portions of the backing layer 16 and generally extends outwardly, at least in part, from the distal surface d of the absorbent core 14 and in relation to the distended portion of the backing layer 16 delimited by the compliant element 26.

It will be understood that the preferred facing layer 12 also has suitable elastic properties to enable it to stretch as the absorbent core 14 expands laterally.

When the dressing 10 has expanded to a maximum capacity, defined as an exudate-laden or fully saturated dressing, it will be desirable to remove and replace the dressing 10. When in a saturated or fully exudate-laden stage, the corners along the border portion 24 of the dressing 10 generally remain adhered to the wound site w despite the excessive uptake of exudate since the facing layer 12 provides sufficient adherence to the skin surrounding the wound site w. By observing the extent of swelling of the dressing in relation to the degree of fluid uptake into the absorbent core and by the absorbent material, one can be visually determine when it is appropriate to remove the dressing.

3. Description of Components of the Wound Dressing

The absorbent core preferably comprises a hydrophilic synthetic polymer conformable to body surfaces and adapted to be capable of absorbing fluid. It is desirable that the absorbent core absorb exudate rapidly so as to enhance its effectiveness in the dressing and, in particular, the fluid uptake to the receptacles containing the absorbent material. In addition to absorption, an effective wicking mechanism is desirable, that is the absorbent core should rapidly direct fluids away from the proximal surface of the absorbent core to more remote areas for storage (i.e., the receptacles containing the discrete portions of absorbent material), so as to minimize local saturation and maximize the efficiency of the absorbent core.

A preferable absorbent core is constructed of flexible open-cell foam that is at least slightly hydrophilic. Suitable foams have an open cell size of 30 to 700 microns, and preferably a cell size of 50 to 300 microns. The open cells permit transport of fluid and cellular debris into and within the foam, and it is preferred that the cell size of areas of the foam be of sufficient size to encourage capillary action and promote fluid transport.

The absorbent core may expand about 135% of its size when saturated with fluid. When combined with the facing and backing layers of the invention, the absorbent core may expand to only about 110% of its dry size when exudate laden.

In accordance with one embodiment of the invention, the absorbent foam comprises a gradient of cell sizes across the thickness of the absorbent core such that the cell size decreases in the direction of the distal surface and of the absorbent core. Since the cell sizes are greater at and near the proximal surface of the absorbent core, the capillary forces are stronger and therefore will drain fluid near the proximal surface of the absorbent core and draw the fluid towards the receptacles. In addition, the absorbent foam may include a cell size gradient that is directed towards the receptacles, thereby providing localized regions in the absorbent foam that are configured to have increased capillary forces and directed towards the receptacles to aid in the guidance of fluid.

The foam may be made, for example, from polyurethane, cellulose, carboxylated butadiene-styrene rubber, polyester foams, hydrophilic epoxy foams or polyacrylate. According to a preferred embodiment, the foam is formed from hydrophilic polyurethane foam, such as polyurethane foam made by Reynel Inc. (Boothbay, Me.) under product designation L00562-B.

It will be understood that the absorbent core is not limited to being constituted of foam. In variations of the embodiments, the absorbent core may be a porous woven or non-woven material that may be produced by any number of means using known materials available to those skilled in the art. For example, the absorbent core may exist as a bulky, loosely formed web composed of very short cellulose fibers arranged in a random or non-random array, a pad of cellulose flakes, or a polymeric fibril matrix.

The thickness of the absorbent core will range from 0.5 mm to 20 mm, and is preferably between 3 mm to 5 mm.

The absorbent core may include an array of receptacles formed therein and may be defined in any suitable preselected pattern that can contain a desired bulk or quantity of discrete portions absorbent material, while maintaining sufficient strength and flexibility suitable for a dressing of the invention. In a preferred embodiment shown in FIG. 1, the pattern of the receptacles 18 is in a grid-like configuration. Preferably, such receptacles have a uniform, predetermined shape and size, and extend across the distal surface d of the absorbent core.

According to one embodiment, the receptacles are positioned in a rectangular pattern, and the receptacles are generally spaced apart 5 mm (measured from the center axis of each receptacle). The depth of each receptacle is generally 4-5 mm, and positioned at least 0.5 mm from the facing layer. The pattern may be tailored to include more receptacles at specific regions of the dressing as opposed to other regions.

The density of receptacles may be modified in accordance with desired fluid uptake properties of the dressing. For example, the central portion of the absorbent core may have more receptacles arranged in a higher density than near the border portion of the dressing. The amount of receptacles at any given region of the absorbent core may be dependent upon the perceived areas of a greater amount of local occurrence of fluid, such as at the central portion, to maximize fluid absorption, and further limit the absorption of fluid at certain areas of the absorbent core such as at the border portion.

As shown in FIG. 2, the receptacles 18 are arranged to open at the distal surface of the absorbent core 14 and extend a distance into the entire thickness thereof. In a preferred embodiment, the receptacles extend a distance $t_1$, short of the entire thickness t of the absorbent core 18, and it is preferred that the receptacles extend a distance 70-90% of the total thickness of the absorbent core 14. It will be understood, however, that in an embodiment of the wound dressing, the receptacles may extend through the entire thickness of the absorbent core.

The depths of the receptacles may be modified according to desired storage of absorbent material that is placed therein. For example, the receptacles may be arranged to extend at different distances into the thickness of the absorbent core on the basis of their location and the local occurrence of fluid exuded from a wound site. According to one variation, the receptacles located closer to the center of the dressing extend deeper into the thickness of the absorbent core and the receptacles closer to the border of the absorbent core extend a shallower distance into the thickness of the absorbent core than the receptacles at the central portion. It follows that the deeper receptacles will contain more absorbent material than the shallower receptacles, and therefore provides a greater localized region of absorption.

Since the receptacles preferably extend only partly into the total thickness of the absorbent core, exudate will be transported to and absorbed by the absorbent material. This effect leaves the proximal side of the absorbent core without the receptacles in a desirably moist environment without excessive saturation of exudate and thus permits the dressing to remain on the wound site for a longer period of time.

The shape of the receptacles is at least partly chosen to maximize the containment of the discrete portions of absorbent material and to facilitate the migration thereof when swollen by fluid. The receptacles are not limited to a cylindrical configuration; the receptacles may take on the shape of pyramids, channels, hemispheres, cones, blocks and truncated variations and combinations thereof. Moreover, the receptacles may include a taper extending from their opening to their base portion so that the receptacles have a greater width near the opening than at the base portion. This configuration facilitates migration of swollen, moisture-laden discrete portions of absorbent material from the receptacles so that they can flow more freely from the receptacles. Alternatively, the receptacles may be arranged in a random pattern along a transverse direction of the distal surface of the dressing.

In a variation of the absorbent core, the receptacles may comprise a plurality of channels extending transversely along at least a portion of the distal side of the absorbent core. In this embodiment, the channels may have a denticulate or an undulating cross-sectional profile. This embodiment may be useful in a wound dressing wherein the absorbent core is too thin to include receptacles having a form such as the aforesaid cylindrical receptacles.

The size of the individual receptacles may be of any suitable size that will contain a suitable amount of absorbent material that will sufficiently absorb exudate from a wound site. Generally, the receptacles are sized from about 500 to 5,000 micrometers, preferably about 1000-3000 micrometers in cross-section (independently height and width dimensions). The receptacles in a preferred pattern have a repeat distance defined as the distance from one receptacle to the next receptacle, center axis to center axis, of 500 to 5,000 micrometers, preferably about 1000-4500 micrometers.

While the receptacles are shown as having a uniform volume across the transverse directions of the wound dressing, the receptacles may have varying volumes depending upon the location of their openings on the distal surface of the absorbent core. As with the embodiment related to the varying depths of the receptacles, the receptacles located at or near the central portion of the absorbent core may have greater volumetric capacity than the receptacles closer to the border portion of the absorbent core. It follows that the receptacles having varying volumes will likewise contain varying bulk amounts of discrete portions of absorbent material.

The absorbent material used in the dressing of the present invention is preferably comprised of superabsorbent polymeric granulates, flakes or powders that swell on exposure to water and form a hydrated gel (hydrogel) by absorbing large amounts of water. Superabsorbents are defined herein as materials that exhibit the ability to absorb large quantities of liquid, i.e., in excess of 10 to 15 parts of liquid per part thereof.

These superabsorbent materials generally fall into three classes, namely starch graft copolymers, cross-linked carboxymethylcellulose derivatives and modified hydrophilic polyacrylates. Examples of such absorbent polymers are hydrolyzed starch-acrylonitrile graft copolymer, a neutralized starch-acrylic acid graft copolymer, a saponified acrylic acid ester-vinyl acetate copolymer, a hydrolyzed acrylonitrile copolymer or acrylamide copolymer, a modified cross-linked polyvinyl alcohol, a neutralized self-crosslinking polyacrylic acid, a crosslinked polyacrylate salt, carboxylated cellulose, and a neutralized crosslinked isobutylene-maleic anhydride copolymer. Superabsorbent particulate hydrophilic polymers also are described in detail in U.S. Pat. No. 4,102,340. That patent discloses absorbent materials such as cross-linked polyacrylamides. Preferably, the super absorbent particles used in the dressing of the present invention are preferably composed of cross-linked poly-acrylic-acid.

Superabsorbent particles are available commercially, for example starch graft polyacrylate hydrogel powders are available from Hoechst-Celanese of Portsmouth, Va. Other superabsorbent particles are marketed under the trademarks SANWET (supplied by Sanyo Kasei Kogyo Kabushiki Kaisha), SUMIKA GEL (supplied by Sumitomo Kagaku Kabushiki Kaisha and which is emulsion polymerized and spherical as opposed to solution polymerized ground particles), and FAVOR (produced by Degussa AG, Duseldorf, Germany).

The super absorbent particles are preferably in the form of granules or flakes to provide a greater available surface area hydrocolloid. The size of the super absorbent particles is typically within the range of 1 to 1000 micrometers when dry. The particle size range of the absorbent particles may be 100 to 900 micrometers. The particles which are insoluble in a wound environment have an absorptive capacity greater than 0.5 of water per gram of dry particles.

Turning to the backing layer, this may be a thin polymeric elastic or flexible film that provides a bacterial barrier formed from a water vapor permeable pliable elastomer material. The film may be continuous in that it has no perforations or pores which extend through the thickness of the film. Films of this type allow water vapor to diffuse therethrough.

According to one variation, the backing layer is bonded to the distal surface of the absorbent core, and does not penetrate any pores, cells or cavities therein. Generally, the film used for the backing and carrier layers is 15 to 45 micrometers in thickness, with a preferred thickness of about 30 micrometers for the backing layer.

The backing layer may comprise polyurethane, such as a polyurethane film available from InteliCoat Technologies (South Hadley, Mass.) under product designation INSPIRE, elastomeric polyester, blends of polyurethane and polyester, polyvinyl chloride, and polyether-amide block copolymer. The preferred backing layer for use in the embodiments described herein is a polyurethane film since it exhibits a resilient property that allows the film to have good conformability and further has a high degree of stretchability.

According to one variation, the backing layer is translucent and, more preferably, sufficiently transparent so that the wound site to which the dressing is applied can be viewed through the dressing. It is advantageous to view to evaluate the wound and healing thereof without removal of the dressing to avoid unnecessary handling of the dressing and exposure of the wound to the environment, which reduces the likelihood of contamination.

Suitable continuous conformable backing layers have a moisture vapor transmission rate (MVTR) of the backing layer alone of 1,500 to 14,600 g/m^2/24 hrs (upright cup test), preferably 2,500 to 2,700 g/m^2/24 hrs at 38° C. The backing layer thickness is preferably in the range of 10 to 1,000 micrometers, more preferably 10 to 100 micrometers.

In reference to the facing layer, the silicone gel layer is preferably hydrophobic, and liquid and moisture impervious. In one variation, the facing layer comprises a cross-linked silicone gel, such as, for example, a cross-linked silicone (polydimethyl siloxane gel) manufactured by NuSil Technology (Carpenteria, Calif.) under product designations MED-6340 or MED-6345 which is tackier than MED-6340.

Alternatively, the facing layer may comprise a silicone gel admixed with a more elastomeric silicone so as to produce a stronger silicone gel compound. For example, MED-6340 can be mixed with MED-4905 (ISR elastomer), which is also produced by NuSil Technology, in a 1:2 ratio to obtain a more cross-linked silicone gel compound. This compound, while losing some of its tackiness, is advantageous because it provides a stronger silicone facing layer while remaining soft to the touch and gentle to wound beds and surrounding areas.

A method used to evaluate adhesion between the different facing layers is to measure the force needed to peel a 25 mm wide sample comprising a silicone gel layer from a stainless steel plate. The differences in the force (measured in N/25 mm) used to remove the sample indicate the difference in the skin adhesion. In the embodiments of the facing layers described herein, the adhesion level on stainless steel of the facing layers range from 1-3 N/25 mm to 0.1-0.3 N/25 mm). It will be noted, however, that the adhesion levels described herein are only exemplary and may be modified according to desired adhesion levels.

The facing layer preferably has a thickness in the range of 0.05 mm to 0.5 mm, and more preferably 0.1 mm. The conformability of the dressing to the wound is somewhat dependent on thickness of the components, such that when the dressing is applied to a body portion, it conforms to the surface even when the surface is moved. When the surface is flexed and then returned to an un-flexed position, the facing layer stretches to accommodate the flexion of the joint but is resilient enough to continue to conform to the surface when the surface is returned to a non-flexed state.

4. Methods for Making the Wound Dressing

Figure 8:
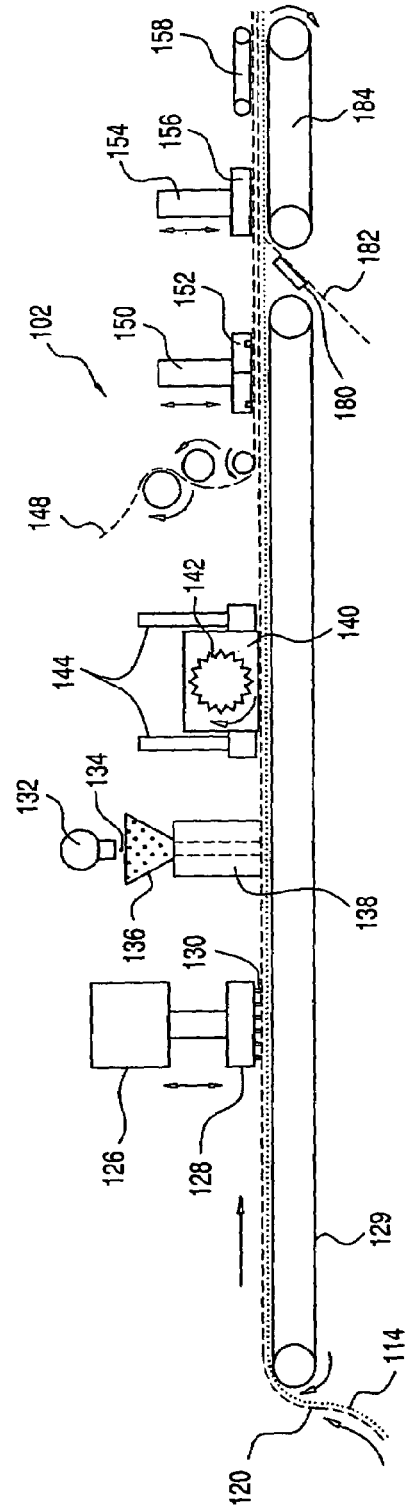

In accordance with manufacturing the embodiments of the wound dressing of the invention, FIGS. 7 and 8 show an exemplary manufacturing model comprising a series of devices for making the wound dressing. The manufacturing model is divided into two main sections: a lamination section 100 shown in FIG. 7, and a finishing section 102 in FIG. 8.

As determined by exhaustive experimentation, one way of making a 10 cm×10 cm dressing is by using a curing temperature for a silicone compound of 160° C., at which the temperature portions of a heated molding surface are maintained; the silicone curing time ("pre-curing") from heating the molding surface to reaching a lamination point (lamination to foam) is about 13 seconds (230 mm/17.9 mms$^{-1}$); the total curing time of the silicone gel film is generally around 2 minutes.

In observing FIG. 7, the method begins by mixing components of a silicone gel compound 102 stored in vats 104 and transported in tubes 106 to an extruder device 108. The extruder device 108 includes an extruding tube 110 that deposits a continuous layer of the silicone gel compound 102 to a moving, molding surface 112. After the silicone gel compound 102 is extruded, it is spread evenly across the width of the molding surface 112 by a spreader arrangement 116 having at least one spreader 118 that is generally oriented at 90° widthwise relative to the molding surface 112.

According to this manufacturing model, the molding surface is preferably in the form of a belt 112 that has a plurality of perforating element extending upright therefrom. Suitable heating elements 124 are provided in the lamination section 100 which are disposed along the path of the belt 112 and, depending on the location of a portion of the belt in the lamination section 100, certain portions of the belt 112 are heated due to exposure to the heating elements 124 to a curing temperature that is suitable for curing the silicone gel compound. The belt 112 preferably travels in the lamination section 100 at a generally constant speed. A suitable release agent, such as TEFLON, is provided across the surface of the belt 112 in order to enable easy. removal of the silicone gel compound 102 therefrom.

Figure 9:
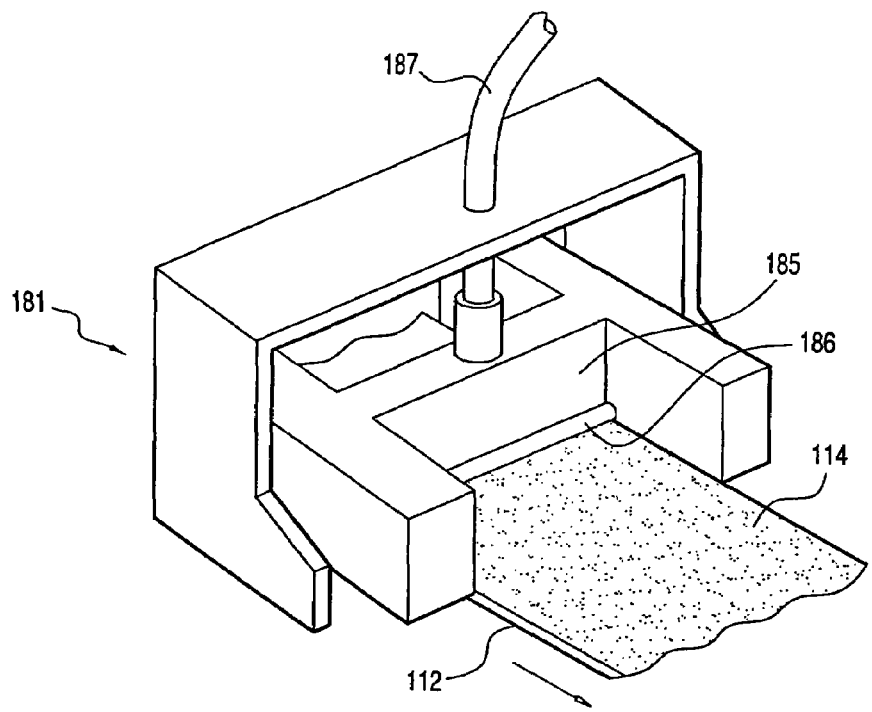
FIG. 9 is a perspective view of an embodiment of an extruder/spreader device.

According to a variation of the embodiment shown in FIG. 7, the extruder device and the spreader arrangement may comprise a single extruder/spreader unit 181 that is illustrated in FIG. 9. This unit 181 preferably comprises an extruding tube 187 that deposits the silicone gel compound onto the belt 112. Following the tube 187 is a spreader 185 carrying a blade 186 that applies constant pressure to the silicone gel compound in order to control the thickness of the thus formed film 114 supported by the belt 112. In other variations, the spreader may comprise a plurality of spreaders, and such spreader blades are preferably silicone rubber blades.

The step of evenly spreading the silicone gel compound transforms the silicone gel compound into a film having a generally uniform thickness. The silicone gel compound is spread about the width of the belt so that the film is generally 0.1 to 0.2 mm thick. By providing a uniform thickness, variables such as curing time and curing temperature are simplified. This contributes to the advantage of having greater control over the parameters for curing the silicone gel compound and laminating the film to the absorbent layer of the wound dressing. Moreover, there is less waste of the silicone gel compound and the openings formed in the thus formed film are more evenly defined.

An important feature of the early steps of the lamination stage of the process is that the film generally begins to cure when portions of the belt carrying the film are exposed to heating elements. While curing of the film may begin as soon as it is carried by the belt, much of the curing of the film is accomplished when the belt is exposed to such heating elements.

Figure 11:
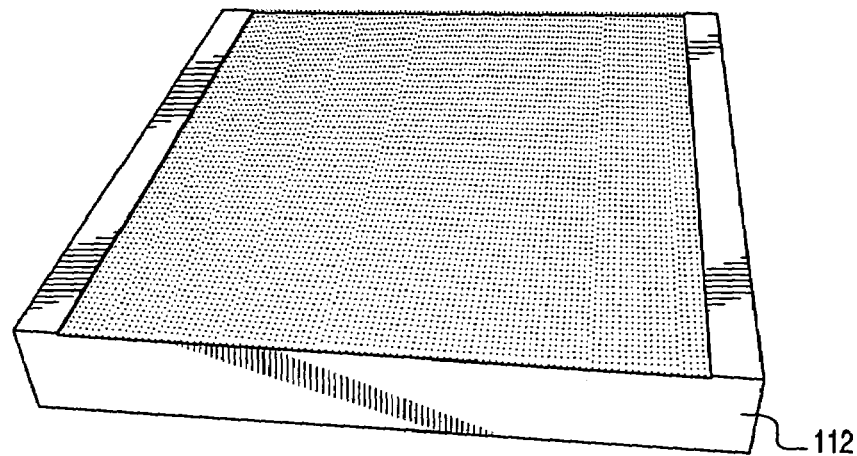
FIG. 11 is a perspective view of an embodiment of a perforation plate for forming apertures in a silicone film.
Figure 12:
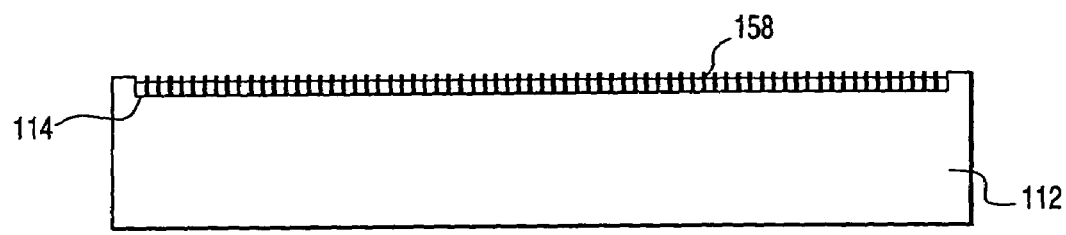
FIG. 12 is an elevational view showing the perforation plate of FIG. 11.

The perforating elements 158, as shown more fully in FIGS. 11 and 12, extend though the entire layer of the film 114. The film 114 cures as the perforating elements 158 form openings across the width of the film 114. The openings in the film 114 are permanently set during the curing of the film as the film travels throughout the laminating section. The perforating elements 158 may be etched from the belt 112 or are connected to belt 112. While the belt 112 is preferably constructed of steel, it may be constructed from a variety of different materials.

The silicone gel compound 102 particularly cures as the belt 112 is exposed to the heating elements to the lamination point 119 whereat it is laminated to the absorbent layer 120. The distance between the point at where the belt 112 is heated to the lamination point 119 is defined by distance $d_2$. By the time the film 114 goes through distance $d_2$, it is partially cured and has transformed to a physical state of a very soft elastic solid. Moreover, the upper surface of the film 114 which is opposite the lower surface disposed along the belt 112 is particularly considered to be partially cured and in a solid state.

At the lamination point 119, a continuous web of the absorbent layer 120, preferably a medical grade, open cell foam, is brought into contact with the upper surface of the partially cured film 114 at a nip area 121 defined between a pressing roller 122 and the moving heated belt 112 carrying the now partially cured and perforated silicone film 114. The film 114 and foam 120 are bonded together at their mating surfaces at the nip area 121 and curing of the film 114 is completed while the film 114 and foam 120 are advanced downstream from the lamination point 119.

Figure 13:
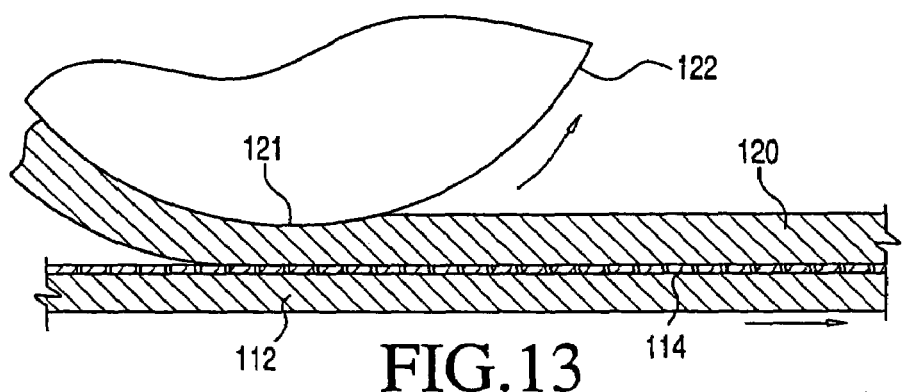
FIG. 13 is an enlarged sectional view showing a laminating point in the lamination section of FIG. 7.

As shown in FIG. 13, the nip roller 122 applies pressure to both the film 114 and the foam 120. The pressure assists in forming a bond between the film 114 and the foam 120 since the cohesive strength of the film 114 might not be sufficient alone to bond to the foam 120 without added pressure. By laminating the film to the foam when the silicone compound is partially cured, the film only bonds to the surface of the foam and completes its curing while adhered to the foam to assure strong adhesion therewith.

All measures are taken to ensure that the film is sufficiently partially cured before the laminating point so that there is no flow of the silicone compound into the open cells of the foam as the foam is laminated with the film. This is controllable because the time for curing of the film is adjustable in the manufacturing process before the lamination step between film and foam. On the other hand, the control over "pre-curing" time ensures that an adequate surface bonding between silicone and foam will occur. In this manner, lamination of the silicone film to the foam is obtained without coating of the end walls of the foam cells by the silicone.

The openings formed in the film by the perforating elements are preferably independent from the location and sizes of the open cells of the foam at the lamination surface, such that the openings can be arranged in any desired pattern as determined by the placement of the perforating elements on the moving belt.

The lamination point 119 is adjustable such that the roller 122 may be adjusted relative to the distance at which the silicone compound 102 is extruded onto the belt 112. For example, the roller 122 may have adjustment means 123, such as a knob, that permits the extension of a bar 125 connected to the roller 122 and a support 127. The bar 125 may have telescoping means or its connection may be adjustable relative to the support 127.

After passing the lamination point 119, the film 114 and foam 120 are transported a distance to enable the film 102 to complete its curing and to assure lamination of the film to the foam. The laminated foam 120 and film 114 proceed to an end of the conveying belt 112 located at wheel 161, are continuously removed from the belt 112, and transported to the finishing section 102. Preferably, there is some slack of the laminated film 114 and foam 120 combination between the lamination section 100 and finishing section 102 in order to accommodate processes that occur in the finishing section 102.

In the embodiment of FIG. 7, the portion of the belt 112 carrying the film 114 is maintained at the curing temperature by the heating element 124 until the silicone laminated foam departs from belt 112. The wheel 161 that drives an end portion of the belt 112 in the lamination section 100 may include at least one heating element 162 provided to maintain such adjacent portion of the belt 112 at the constant curing temperature of the film 114.

The remainder of the belt 112 whereat there is no film 114 cools down to a temperature around 20° C. before it returns to the extruding device 108. The belt 112 is preferably cooled with a cooling element 160 which assists in bringing the temperature down to the desired temperature. It follows that as portions of the belt 112 pass over the heating element 124, such portions rise in temperature to the curing temperature of the film 114 and the pre-curing of the film begins; the pre-curing subsequently ending when the film 114 is laminated onto the foam 120.

In accordance with one variation of the lamination section, as exemplified in FIG. 10, the moving belt 112 is positioned so as to rise towards the roller 122 to an apex 113, and subsequently fall from the apex 113 as the film 114 and foam 120 are laminated to one another. The apex 113 is generally defined as the lamination point. This variation is provided to make the belt 112 as flat as possible so that it is in as much contact with the heating element 124 as possible.

It was determined that this arrangement imparts tension to the belt thereby creating a more even cross-section of the belt, and mitigates or prevents the belt from forming a wavy or rippled profile. This further leads to more uniform curing of the film.

Figure 10:
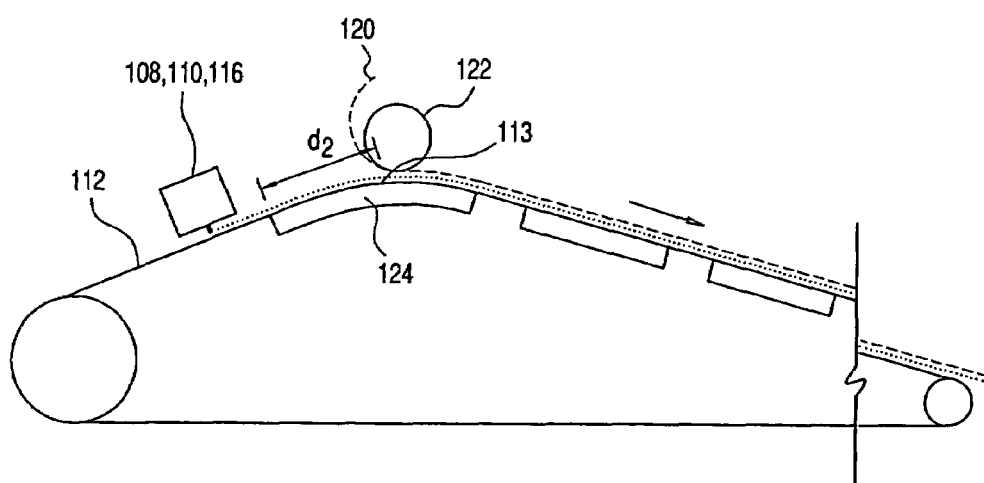
FIG. 10 is an elevational view showing a variation of the lamination section according to FIG. 7.

Of particular note in the variation of FIG. 10, the heating element 124 has a radius that tangentially contacts the belt 112. By this arrangement, the heating element 124 comes into even contact with the belt 112 so that there is substantially uniform temperature profile imparted across the width of the belt 112 and the belt is maintained in tension.

Unlike the lamination section 100, the finishing section 102 includes a belt 129 that transports the laminated film 114 and foam 120 intermittently in a start-stop arrangement so as to enable finishing of the wound dressing with presses 126, 150 and 154. The belt 129 is driven so that it stops under each of the presses 126, 150 and 154. The belt 129 may be coated with polyethylene, TEFLON or other suitable coatings to prevent destruction of the film 114 as it is transported by the belt 129 past the presses 126, 150 and 154 and subsequently removed from the belt 129.

Figure 14:
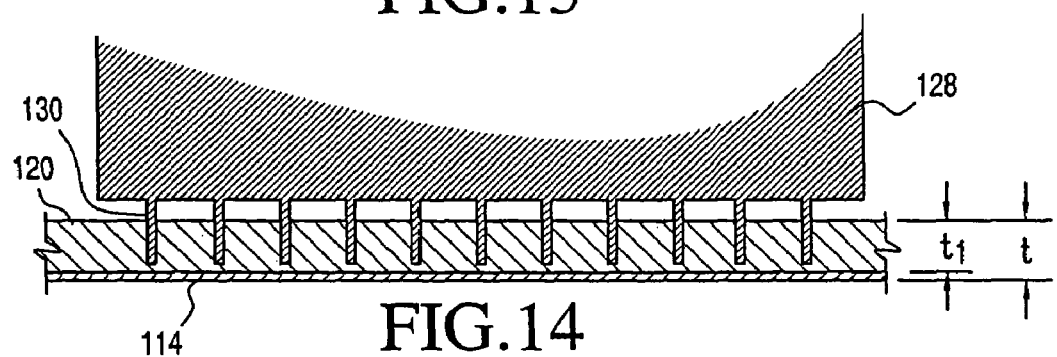
FIGS. 14 and 15 are schematic views showing an arrangement for forming receptacles in an absorbent core in the finishing section of FIG. 8.
Figure 15:
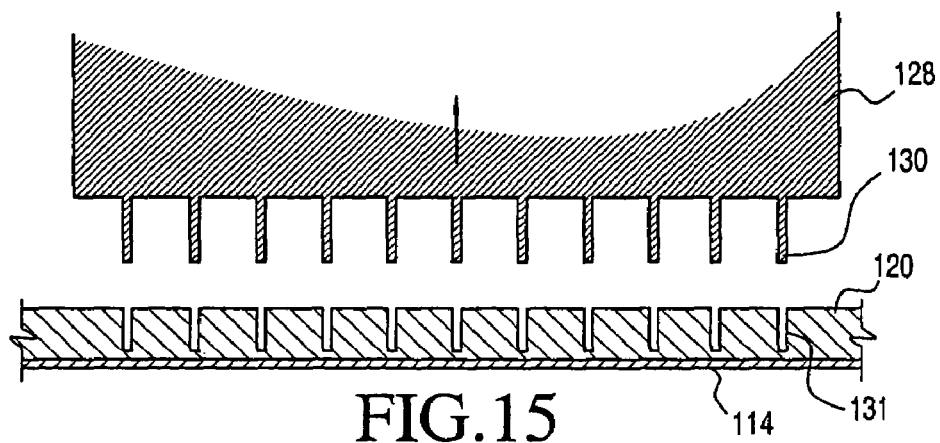

As shown in FIGS. 14 and 15, the first press 126 is provided for forming the receptacles in the foam 120. The press 126 includes a head 128 carrying a plurality of projection elements 130 that are heated to a suitable temperature and are inserted into a surface of the foam 120. The projection elements 130 are heated to a temperature in the range of 200-300° C., preferably 255° C. The projection elements 130 extend into the foam 120 a distance ti less than its total thickness t. According to another variation, the receptacles may be formed by using a hot air stream that imparts a cylindrical shape in the foam.

The projection elements 130 are preferably arranged in a pattern bearing the negative impression of the receptacles 131 of the foam 120. The projection elements 130 are removed from the foam 120 after a period of time, thereby forming the receptacles 131 with the foam 120.

After the receptacles 131 are formed, the receptacles are filled with the absorbent material. According to this variation, the absorbent material is a hydrophilic superabsorbent powder. A supply chamber 132 deposits superabsorbent powder 134 into a funnel 136 that connects to a first chamber 138 in close proximity to the upper surface of the foam 120. The powder 134 falls into the receptacles as the foam 120 is transported past the first chamber 138. It is sufficient to allow the powder 134 to drop onto the foam 120 without any additional assistance in supplement to gravity.

By allowing the powder 134 drop into the receptacles, the powder is loosely retained by the receptacles in order to facilitate the absorption by the powder of fluid and wound exudate. This in turn allows the absorbed powder to migrate from the receptacles upon absorption of such fluid and exudate. However, if indeed it is desired that the powder be compacted, the powder may be mechanically urged into each of the receptacles by elements corresponding to the receptacles, or by air injection.

After the foam 120 passes past the first chamber 138, the surface of the foam 120 is wiped by a rotating brush 142 located in a second chamber 140. The rotating brush 142 wipes the surface of the foam 120 to remove any stray powder 134 located on the foam surface. As the brush 142 wipes the surface of the foam 120, a vacuum 144 sucks the wiped powder out of the second chamber 146 so that the surface of foam is devoid of powder. After the receptacles are filled with super absorbent powder, the foam 120 is prepared for the lamination of a backing layer.

The laminated foam 120 is next transported underneath a platen 152 connected to a press 150. The belt stops as the platen 152 is urged against the foam to partially laminate the backing layer 148 thereto and form a compliant element thereon.

After the backing layer 148 is secured to the foam, a cutting press 154 carrying a cutting die 156 is used to cut the shape of the wound dressing from the thus laminated combination of film 114, foam 120 and backing layer 148.

An example of a suitable platen 152 and cutting die 156 is described in U.S. patent application Ser. No. 10/725,574 which describes a platen singly arranged for laminating a backing layer to foam, forming the compliant feature and cutting the shape of the wound dressing. While the platen in U.S. patent application Ser. No. 10/725,574 is described as comprising both a profiled surface for laminating and forming the compliant element, and cutting edges, multiple platens may be used to perform separate tasks. This is exemplified in FIG. 8 wherein the platen 152 performs the laminating and compliant element forming features, and the cutting die 156 cuts the shape of the wound dressing.

As shown in FIG. 8, a release paper 182 is applied to the surface of the film 114 prior to the cutting of the wound dressing by the cutting die 156. The release paper is regulated by a feeding device 180 that is provided to operate in combination with a speed regulating device 158. The belt 129 terminates prior to the feeding device 180, wherein belt 184 follows the feeding device 180 and terminates shortly after the speed regulating device 158. The speed regulating device 158 monitors the speed and motion of the belt 129 so that foam 120 is properly located under each of the presses 126, 150 and 154.

5. Experimental Information

In connection with the inventive embodiments and methods for making the embodiments in the aforesaid discussion, various experimental data has been obtained to ascertain proper parameters for obtaining the embodiments of the invention.

In the following discussion, experimental data will be discussed in view of the parameters involved in the inventive aforesaid methods. In studying this data, scanning electron microscope (SEM) images were taken for each sampling of dressings in accordance with parameter changes. These SEM images enabled a determination as to the adhesion of the silicone film to the foam, and further served as an indicator as to whether the silicone film was drawn into holes defined by the foam. In addition, visual inspection of the dressings and manual manipulation of the silicone film enabled a determination as to the level of adherence of the silicone film to the foam.

Various parameters are involved in laminating the silicone film to the foam. The following fixed parameters were maintained constant during the course of the study:

| Parameter | Description | Values during experiment | Estimated uncertainty |
|---|---|---|---|
| P | Pressure on spreaders | 3.3 kg. | 20% |
| m | Mass of pressing roller | 1320 g | 2% |
| τ | Pressure on conveyor belt | 2 | |
| s | Tension of the foam | 75 g | 40% |
| r | Ratio of gel components MED-4905 (ISR elastomer) and MED-6340 | 2:1 | 2% |
| b | Silicone part A and B mixing ratio | 1:1 | <0.5% |

The purpose of the study was to identify upper and lower limits for the temperature of the heating elements and the pre-curing distance of the silicone film prior to lamination with the foam. The study involved various different values for the curing temperature of the heating elements $T_c$, and the pre-curing distance $d_1$ at such various values for the curing temperature $T_c$.

The study required determining certain limits for pre-curing distance $d_1$. The lower limit $d_{1\ min}$ is determined when the silicone film is drawn into the holes of the foam. This results in "impregnation" of the foam by the film. This occurs when capillary forces draw the silicone film into the foam since the silicone film has likely not sufficiently cross-linked to resist such capillary forces.

The upper limit $d_{1\ max}$ is determined when the silicone film does not sufficiently adhere to the foam. This results in a "loose" film. This occurs when the silicone gel cross-linked too much prior to the lamination of the silicone film to the foam, and has failed to adhere thereto.

In summary, a positive result is obtained if the distance $d_1$ falls within the range of $d_{1\ min}$ and $d_{1\ max}$. Obviously, a negative result is obtained if the distance d falls outside of the range of $d_{1\ min}$ and $d_{1\ max}$.

As a side, the pressure P exerted by the spreaders to spread the silicone film evenly onto the belt may be adjusted since it is used to control the degree of openness of the apertures of the silicone film. A pressure of 3.3 kg to 4.2 kg may be used to effectively imparting the pattern of apertures in the silicone film having a thickness of 0.1 mm.

In the study, a 10 cm×10 cm dressing was used to obtain the proper limits for the curing temperature $T_c$, and the pre-curing distance $d_1$. Of course, different sized dressings will require different ranges for both the curing temperature $T_c$ and the pre-curing distance $d_1$.

As a result of the study, the following ranges were obtained:

| Curing temperature $T_c$ (° C.) | $d_{max}$ (mm) | $d_{min}$ (mm) | Δd (mm) |
|---|---|---|---|
| 130 | 360 | 350 | 10 |
| 140 | 300 | 290 | 10 |
| 160 | 235 | 220 | 15 |

Subsequent experimental data has shown that with a conveyor velocity v of 15 mm/s, a curing temperature $T_c$ of 160° C. and a pre-curing distance $d_1$ of 210 mm, a 10 cm×10 cm dressing of the type of the invention may be successfully obtained which avoids both impregnation of the foam by the silicone film, and a silicone film that securely laminates to the foam. For a longer dressing, such as a 10 cm×20 cm dressing, the parameters for curing the silicone film change wherein the conveyor velocity v is 27.8 mm/s, the curing temperature $T_c$ is 160° C. and the pre-curing distance $d_1$ is 290 mm.

It will be understood that the methods according the invention are not limited to using the parameters described herein, but may be adjusted to obtain pre-curing distances $d_1$ that fall within the range of $d_{1\ min}$ and $d_{1\ Max}$. Moreover, the embodiments of the invention are not limited to being manufactured solely by the methods described herein, but instead may be manufactured in any manner that will obtain a dressing having a silicone film laminated onto foam which avoids both impregnation of the foam by the silicone film, and a silicone film that securely laminates to the foam.

It will also be understood that the above described embodiments of the invention are illustrative in nature, and that modifications thereof may occur to those skilled in the art. Accordingly, this invention is not to be regarded as limited to the embodiments disclosed herein, but is to be limited only as defined in the appended claims.

We claim:

1. A laminated structure comprising:
   a porous web defining first and second opposed sides, the first side having a plurality of surface irregularities;
   a polymeric film having opposed first and second surfaces, the second side being laminated onto and coextensive with the first side of the porous web, the polymeric film having a generally uniform thickness and a plurality of molded apertures arranged in a pattern;
   wherein the apertures of the polymeric film are formed independently from the surface irregularities of the porous web;
   wherein the polymeric film comprises a silicone gel.

2. The laminated structure according to claim 1, wherein the apertures of the polymeric film are generally uniformly spaced from one another.

3. The laminated structure according to claim 1, wherein the apertures of the polymeric film are generally uniformly sized.

4. The laminated structure according to claim 1, wherein the porous web is a foam having a plurality of pores.

5. A laminated structure comprising:
   a porous web defining first and second opposed sides, the first side having a plurality of surface irregularities;
   a polymeric film having opposed first and second surfaces, the second side being laminated onto and coextensive with the first side of the porous web, the polymeric film having a generally uniform thickness and a plurality of molded apertures arranged in a pattern;
   wherein the apertures of the polymeric film are formed independently from the surface irregularities of the porous web;
   wherein the polymeric film comprises a mixture of a silicone elastomer and a silicone gel in a predetermined ratio.

6. The laminated structure according to claim 5, wherein the apertures of the polymeric film are generally uniformly spaced from one another.

7. The laminated structure according to claim 5, wherein the apertures of the polymeric film are generally uniformly sized.

8. The laminated structure according to claim 5, wherein the porous web is a foam having a plurality of pores.

* * * * *